United States Patent
Zelickson et al.

(10) Patent No.: US 8,052,662 B2
(45) Date of Patent: Nov. 8, 2011

(54) SKIN ABRASION SYSTEM AND METHOD

(75) Inventors: Brian D. Zelickson, Minneapolis, MN (US); David A. Kist, Hopkins, MN (US); Mark A. Rydell, Golden Valley, MN (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 12/098,844

(22) Filed: Apr. 7, 2008

(65) Prior Publication Data
US 2009/0234304 A1    Sep. 17, 2009

Related U.S. Application Data

(63) Continuation of application No. 10/344,064, filed as application No. PCT/US01/04201 on Feb. 9, 2001, now Pat. No. 7,354,423, which is a continuation-in-part of application No. 09/635,285, filed on Aug. 9, 2000, now Pat. No. 6,645,184.

(60) Provisional application No. 60/147,916, filed on Aug. 9, 1999.

(51) Int. Cl.
*A61M 35/00* (2006.01)
*A46B 13/00* (2006.01)

(52) U.S. Cl. .................. 604/289; 604/290; 606/131

(58) Field of Classification Search .................. 604/289, 604/290; 606/131; 601/70, 80, 87, 93, 141, 601/150; 15/22.1
See application file for complete search history.

(56) References Cited

U.S. PATENT DOCUMENTS

| | | | | |
|---|---|---|---|---|
| 3,699,952 A | * | 10/1972 | Waters et al. | 601/18 |
| 4,040,414 A | * | 8/1977 | Suroff | 601/2 |
| 4,192,035 A | * | 3/1980 | Kuris | 15/22.1 |
| 4,291,685 A | * | 9/1981 | Taelman | 601/17 |
| 4,408,623 A | | 10/1983 | Murray | |
| 4,422,465 A | | 12/1983 | Haga | |
| 4,447,482 A | | 5/1984 | Heinzelman et al. | |
| 4,513,737 A | | 4/1985 | Mabuchi | |
| 4,572,187 A | | 2/1986 | Schetrumpf | |
| 4,643,207 A | | 2/1987 | Grahame | |
| 4,698,869 A | * | 10/1987 | Mierau et al. | 15/22.1 |
| 4,752,472 A | | 6/1988 | Kligman | |
| 5,033,485 A | | 7/1991 | Hauerwas et al. | |
| 5,037,432 A | | 8/1991 | Molinari | |
| 5,224,469 A | * | 7/1993 | Mocny | 601/108 |
| 5,383,900 A | | 1/1995 | Krantz | |
| 5,493,747 A | * | 2/1996 | Inakagata et al. | 15/22.1 |
| 5,685,833 A | | 11/1997 | Turngren | |
| 5,720,963 A | | 2/1998 | Smith | |
| 5,759,093 A | | 6/1998 | Rodriguez | |
| 5,800,446 A | * | 9/1998 | Banuchi | 606/131 |
| 5,935,596 A | | 8/1999 | Crotty et al. | |
| 5,964,749 A | | 10/1999 | Eckhouse et al. | |
| 5,971,999 A | | 10/1999 | Naldoni | |

(Continued)

FOREIGN PATENT DOCUMENTS
DE    8304519 U1    6/1983
(Continued)

*Primary Examiner* — Jacqueline F Stephens

(57) ABSTRACT

A system and method for rejuvenating skin through ablation using a handheld device (200) having a removable treatment component (213) with an abrasive material on one surface of the component which surface is on a portion of the treatment component (213) configured to conform to a skin surface. The system further includes application of other elements to facilitate skin recovery and rejuvenation processes.

14 Claims, 8 Drawing Sheets

U.S. PATENT DOCUMENTS

| | | | |
|---|---|---|---|
| 6,039,745 A | 3/2000 | Di Fiore et al. | |
| 6,080,165 A | 6/2000 | DeJacma | |
| 6,106,818 A | 8/2000 | Dulog et al. | |
| 6,113,559 A | 9/2000 | Klopotek | |
| 6,136,008 A | 10/2000 | Becker et al. | |
| 6,136,200 A | 10/2000 | Waldmann | |
| 6,139,553 A * | 10/2000 | Dotan | 606/131 |
| 6,221,382 B1 | 4/2001 | Ishida et al. | |
| 6,228,487 B1 | 5/2001 | Howard et al. | |
| 6,241,739 B1 * | 6/2001 | Waldron | 606/131 |
| 6,277,128 B1 * | 8/2001 | Muldner | 606/133 |
| 6,355,007 B1 * | 3/2002 | Zuckerbrod | 601/72 |
| 6,391,034 B1 * | 5/2002 | Adamson et al. | 606/131 |
| 6,645,184 B1 * | 11/2003 | Zelickson et al. | 604/290 |
| 6,692,505 B1 * | 2/2004 | Maier et al. | 606/131 |
| 6,848,451 B2 | 2/2005 | Postal et al. | |
| 2003/0093089 A1 * | 5/2003 | Greenberg | 606/131 |
| 2005/0143754 A1 * | 6/2005 | Zelickson et al. | 606/131 |

FOREIGN PATENT DOCUMENTS

| | | |
|---|---|---|
| DE | 9312913 U1 | 10/1993 |
| DE | 29803828 U1 | 9/1998 |
| DE | 19733501 A | 2/1999 |
| FR | 2063743 A | 7/1971 |
| FR | 2773461 A | 7/1999 |
| JP | 61293462 A | 6/1985 |
| JP | 1989-101401 U | 7/1989 |
| JP | 1212507 A | 8/1989 |
| JP | 562238 U | 1/1992 |
| JP | 1993-039404 U | 5/1993 |
| JP | 3000144 U | 5/1994 |
| JP | 6328042 A | 11/1994 |
| JP | 9238745 A | 9/1997 |
| JP | 3053069 U | 7/1998 |
| JP | 2000060927 A | 2/2000 |
| WO | WO 00/15300 A | 3/2000 |

* cited by examiner

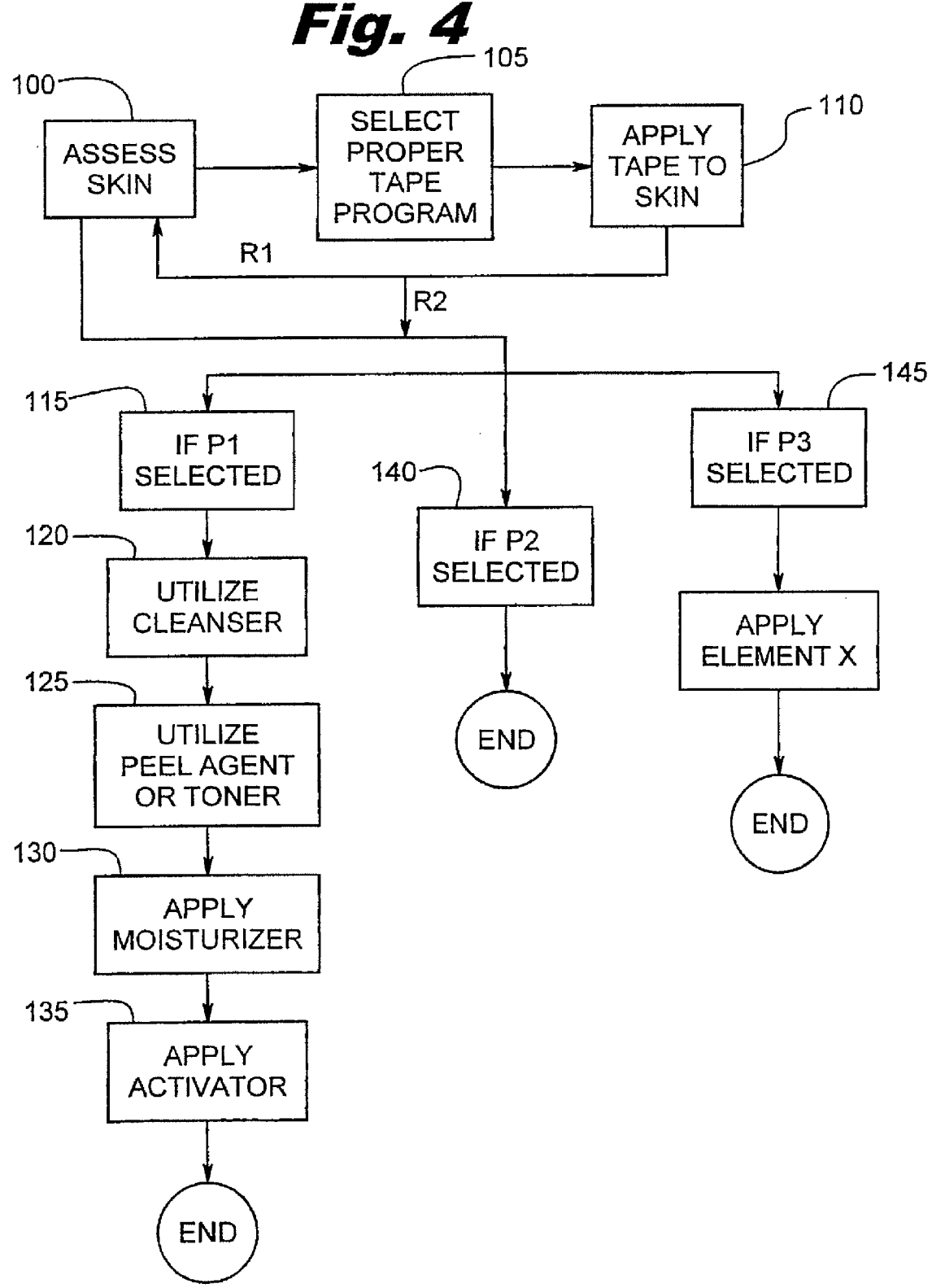

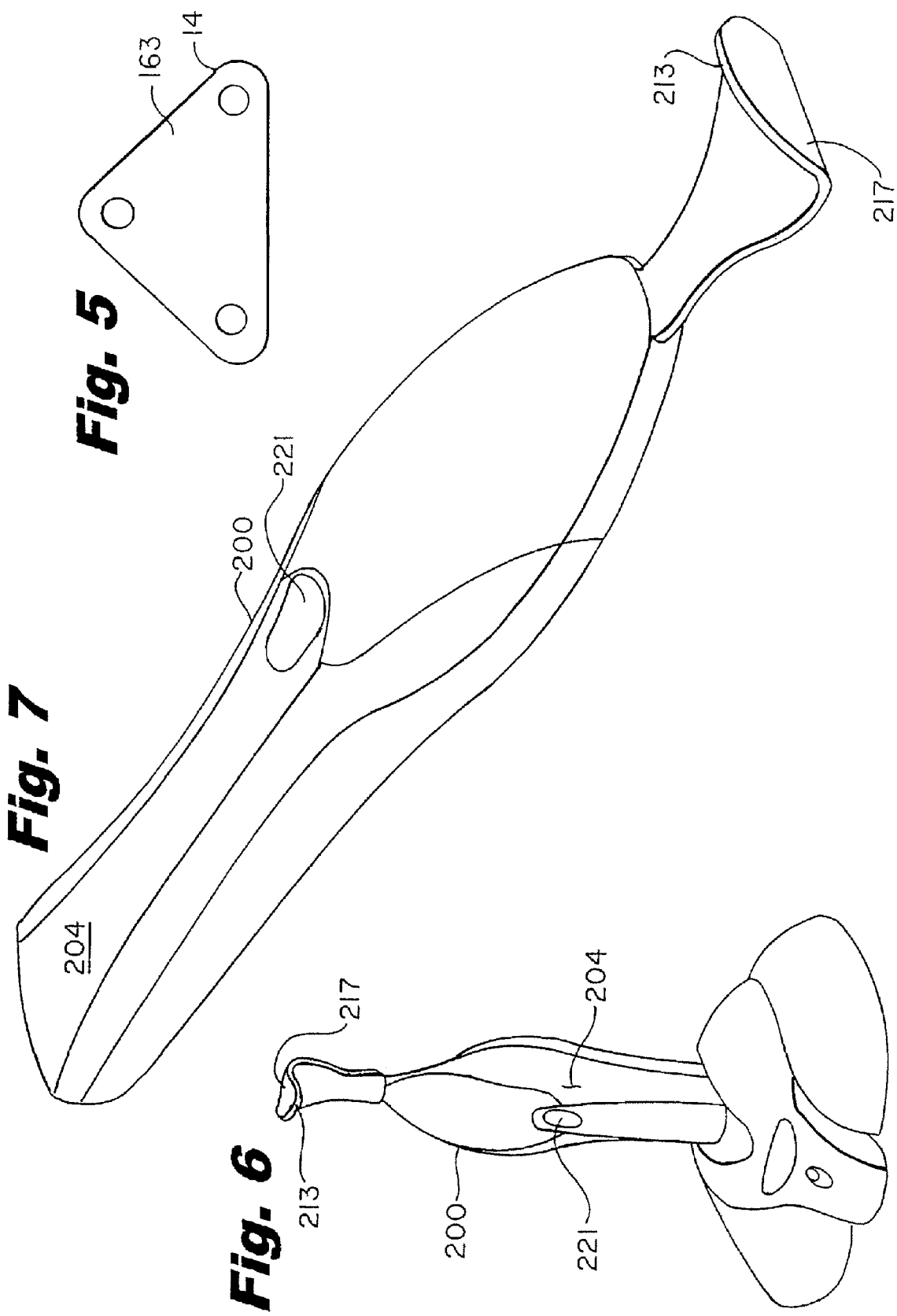

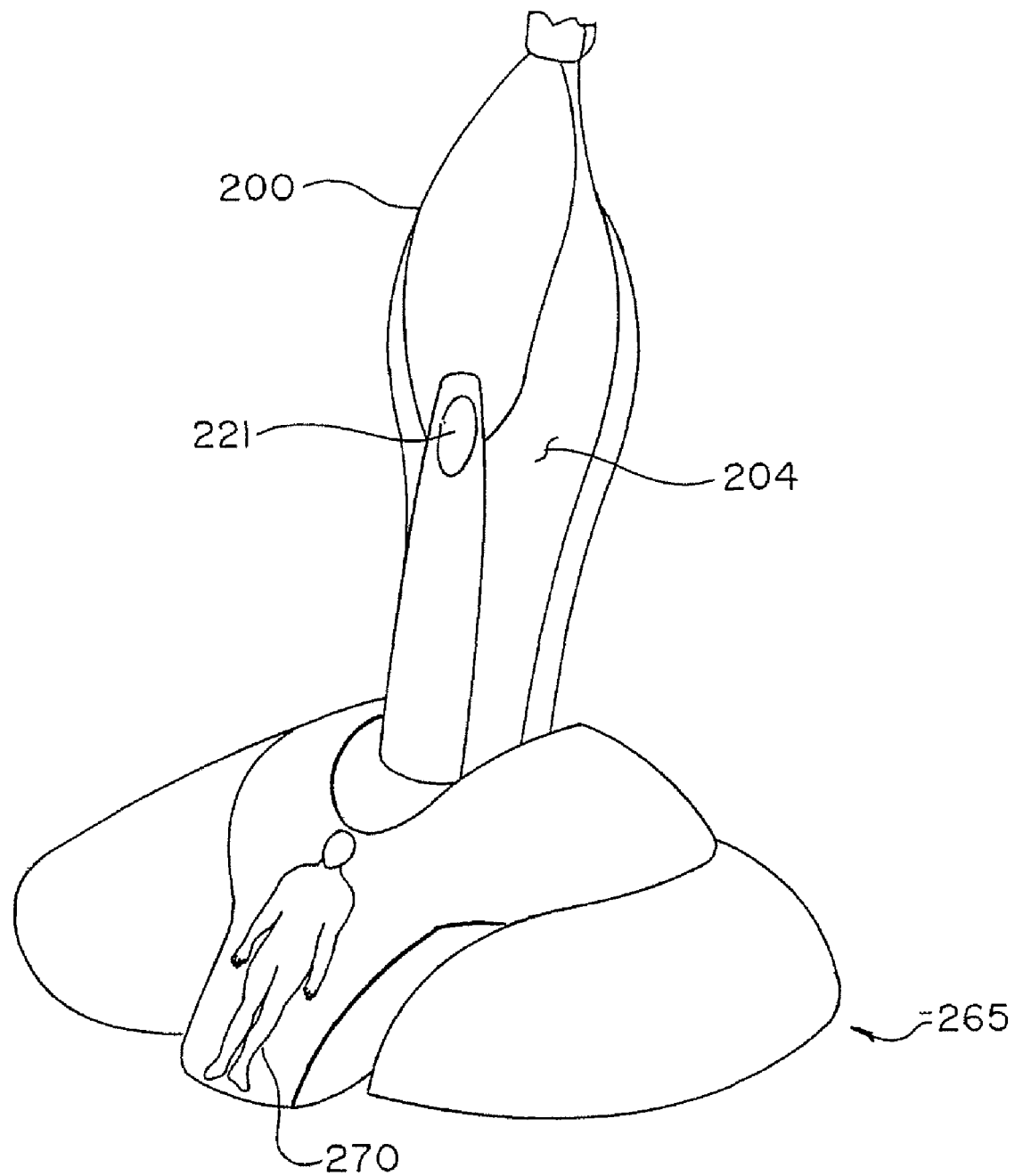

SKIN ABRASION SYSTEM AND METHOD

CROSS-REFERENCE TO RELATED APPLICATIONS

This application is a continuation of application U.S. Ser. No. 10/344,064 filed Jun. 18, 2004, now U.S. Pat. No. 7,354,423 which is the national stage filing under 35 USC 371 of international application PCT/US01/04201 filed Feb. 9, 2001, which is a Continuation-in-Part-of U.S. Ser. No. 09/635,285 filed on Aug. 9, 2000; now U.S. Pat. No. 6,645,184, which claims the benefit of U.S. Provisional Ser. No. 60/147,916 filed Aug. 9, 1999. The complete disclosures of the aforementioned related patent applications are hereby incorporated herein by reference for all purposes.

FIELD OF THE INVENTION

The invention relates to apparatus and methods for abrading, cleaning and rejuvenating skin.

BACKGROUND OF THE INVENTION

Various environmental and natural occurrences result in blemishes and wrinkles to human skin. For example, sun exposure, chronic irritation due to many different causes, and neglect may all cause skin problems. Recent advances in laser and chemical treatments have been successful in improving the appearance of the treated skin but these methods are rather labor intensive and can be traumatic.

One approach by medical practitioners includes the use of micro-dermabrasion techniques to treat skin blemishes. Although quite effective in certain applications, this technique can be risky and requires specially licensed operators.

Another approach by medical and cosmetic practitioners includes the use of adhesive-type tape applied to the patient's skin so that when the tape is removed the tape also removes an upper portion of the skin. This form of procedure is referred to as barrier disruption. Some analyses have suggested that barrier disruption by cellophane tape stripping triggers a cascade of biochemical activity which serves to "turn over" structural proteins that constitute human skin. For example, such tape stripping may stimulate the production of keratins 6,16,17 and reduce the mount of keratins 5 and 14, while also prematurely expressing involucrin. Yet another analysis suggests that tape stripping increases the rate of transepidermal water loss by 100 times the normal rate. In yet another analysis, tape stripping is suggested as having a regulatory effect upon fatty acid transport proteins and fatty acyl CoA synthase.

This data suggests that biochemical activity occurs following tape stripping which may be related to long term skin restructuring. An immediate consequence is the removal of redundant scale, plaques, and comedones which results in a rejuvenated appearance.

Recently, a lot of effort of dermatologists and skin care specialists has been focused on developing methods for the prevention and treatment of photo-aging skin. Methods for preventing photo aging include sun protection and avoidance and the use of anti-oxidants in diet and applied topically to the skin.

Methods of treating sun damaged or aging skin include drug treatments with retinoids, anti-oxidants, biologicals and other compositions and treatments using devices or materials such as ablative treatments, which removes tissue from the surface of the skin through to the epidermis and in some cases to the dermis layers of the skin, non-ablative treatments, which include dermal stimulation, and minimally ablative treatments which removes tissue from the stratum corneum layer of skin. Some examples of aggressive ablative methods that are used to even out skin color, lines and remove pre-cancerous lesions by removing portions of the epidermis and/or dermis include dermabrasion using a dermabrader, a rapidly rotating device is used to remove the upper layers of the skin, laser abrasion or laser resurfacing using either $CO_2$ laser or an erbium YAG laser, which burns the outer layer of the skin with a controlled second degree burn, or phenol or trichloroacetic acid peels. Each of these aggressive ablative methods results in skin damage. With dermabrasion and laser abrasion, the skin will remain red or pink for weeks to months, with peels depending upon the type of peel the skin will look red for one week to months.

Less aggressive methods for superficial exfoliation have been developed which include superficial chemical peels, which use alpha hydroxyacids found in fruits and other foods and microdermabrasion which consist of a machine which blasts the skin with very fine particulate matter. These less aggressive methods also result in skin redness and require multiple methods.

SUMMARY OF THE INVENTION

A tape roller is provided for a user to self-administer the tape to portions of the user's skin. This facilitates the removal of elements of the skin and facilitates self-administration of other skin agents or to simply improve the health or appearance of the user's skin. A system and method of integrated skin care is provided which relies on the effective and easy removal of upper skin detritus.

In another embodiment, a system and method of integrated skin care is provided which relies on the effective and easy removal of upper skin detritus resulting in less redness and edema than microdermabrasion and with proper instruction, treatments can be carried out by the individual being treated rather than having all the treatments performed by a professional skin care specialist. The system of the invention includes a handheld device including an internal motion generator and a removable treatment component having a first portion designed for connection with the internal motion generator of the apparatus and a second portion having a shaped configuration and a first and second surface, wherein the second portion is configured so that the first surface will conform to a skin surface and wherein said first surface comprises an abrasive material formed in or attached to the surface, wherein the abrasive material is chosen for its ability to clean, abrade, or polish the skin surface when moved over the skin surface.

BRIEF DESCRIPTION OF THE DRAWINGS

FIG. 4 is a diagram depicting a preferred system and methodology for administration of skin care using the tape removal concept of this invention.

FIG. 5 is a bottom plan view of a tape dispenser. FIG. 6 is a perspective view of an embodiment of the invention, with a charging unit.

FIG. 7 is a perspective view of an embodiment of the invention.

FIG. 13 is a perspective view of an embodiment of a stand of the invention showing a display.

DETAILED DESCRIPTION

Figure 1:
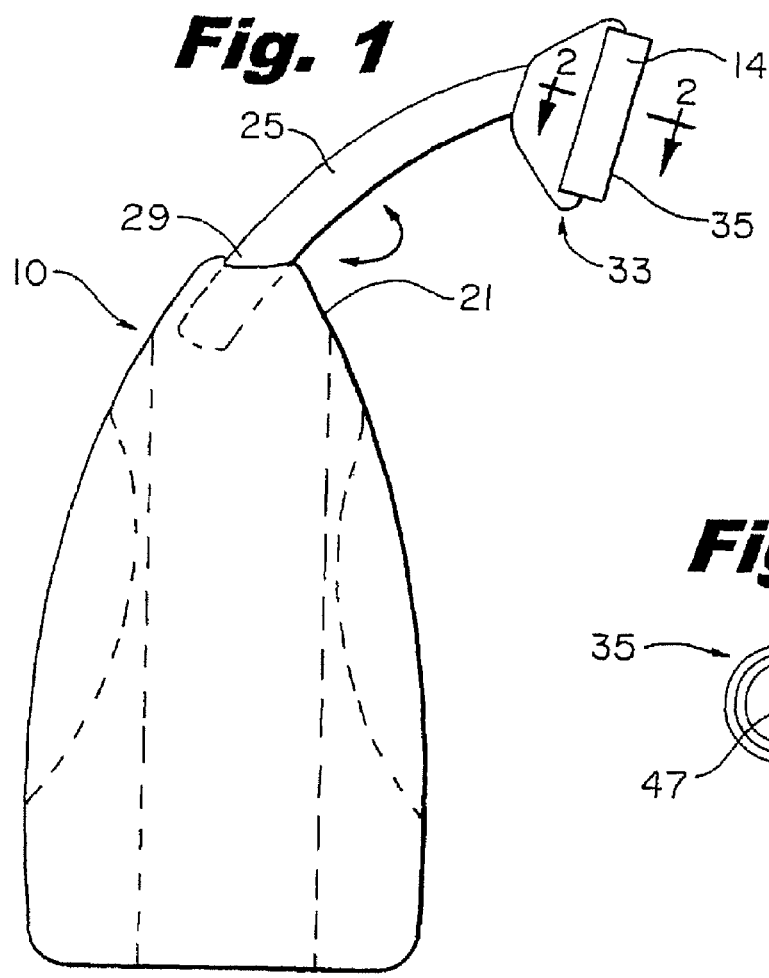
FIG. 1 is a perspective view of a handheld apparatus for self-administration of tape to skin.

FIG. 1 is a perspective view of a handheld apparatus 10 for self-administration of a tape-like product 14 to skin. Apparatus 10, also referred to as system 10, includes, in one embodiment, a handheld ergonomically structured device 21. Handheld device 21 comprises a body portion having a variety of optional shapes and configurations, as depicted by representative dashed lines, although not limited to said precise configurations. Most importantly, the body portion shape must conform to a comfortable gripping configuration of a user's hand when using the device for self-administration at or about the facial area, as well as other body portions. For this reason, it is recognized that extension 25 may be formed as a unitary part with the body portion, or it may be separately attached and/or inserted at various locations on body portion, such as at neck 29, or other locations. Suitable attaching and locking means are contemplated in the event that extension 25 forms a piece separate than the body portion. Regardless, a tape dispensing holder is positioned at a distal end 33 of extension 25. This feature comprises any of various retaining means suitable for holding and dispensing a rolled tape unit 35. It is appreciated that extension 25 may be made of a material that has a memory suitable for reconfiguring by each user, possibly through use of advanced technology material such as that similar to a nitinol-type of material or one with suitable reshaping characteristics, or it may be simply be manufactured to have a curvilinear or other shape suitable for a single design optimized for all users.

Figure 2:
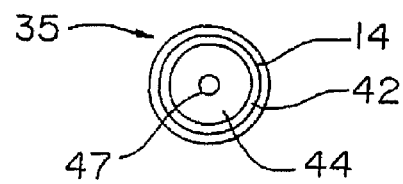
FIG. 2 is a section view of a tape roll taken along lines 2-2 of FIG. 1.

As shown in FIGS. 1 and 2, rolled tape unit 35 comprises a cylindrical-style roll of material forming at least one outer layer of tacky material, referred to here as tape. The outer tacky material of rolled tape unit 35 is designed for dispensing along the surface of the user's skin, preferably facial skin, in order to remove detritus and other undesired material from the surface of the skin. Indeed, according to the various programs of usage and degree of tackiness of the tape, it is possible to remove both scales and external environmental pollutants as well as portions of the skin itself. In one embodiment it is also conceivable to have multiple layers of tape, for example, as shown in FIG. 2 at layer 42. In this embodiment it is possible to utilize the same rolled tape unit 35, but extend its life by removing a used outer layer of tacky tape material 14 and exposing an unused tacky layer of tape material 42 for subsequent use, or at the subsequent use time. Layer or volume 44 of rolled tape unit 35 may simply comprise additional layers of tape or it may provide a spacer having various material properties. For example, one type of spacer may include a resilient material to reduce the rigidity and increase the tactile affection of the user and the product being applied to the user's skin.

Either a dimple or full channel may comprise the most efficacious means of allowing the rolled tape unit to function along with the distal end dispensing portion of the handheld device. Such dimple or channel is represented by element 47 in FIG. 2.

Figure 3:
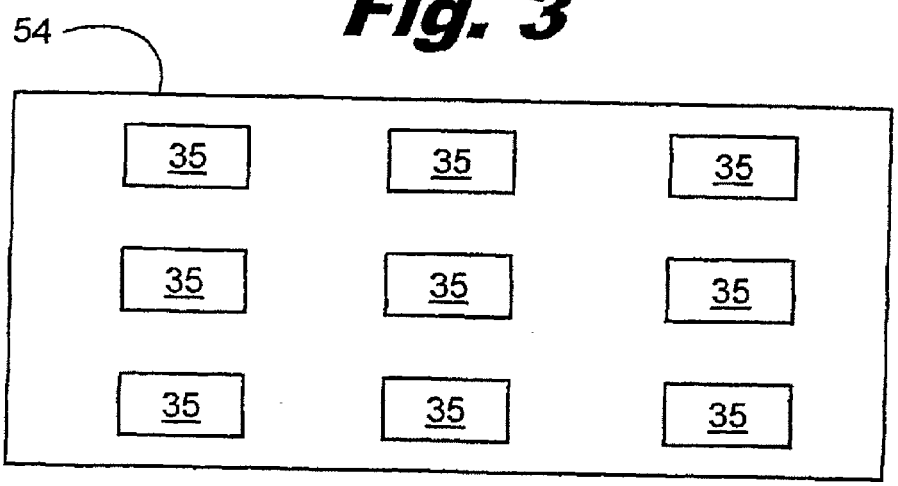
FIG. 3 is a plan view of an exemplary dispenser of tape rolls.
Figure 8:
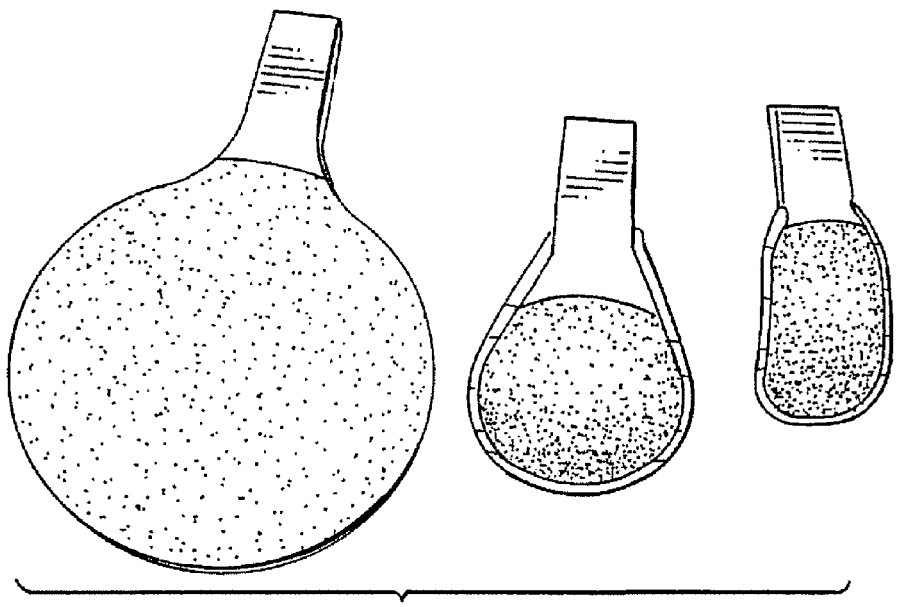
FIG. 8 is a plan view of three sizes of removable treatment components of the invention.

FIG. 3 discloses dispensing pack 54 designed for holding and dispensing one or more rolled tape units 35. In one embodiment, dispensing pack 54 may be structured with opening and closure layers similar to those packages known in the dispensing industry as blister packs. In this embodiment, the user simply presses on one side of dispensing pack 54 to release a single rolled tape unit 35 from the package. In that instance it is important that a cover layer (which is retaining the rolled tape unit within the package) to have a material or material coating suitable to prevent adherence to the rolled tape unit tacky layer. Alternatively, a non-tacky cover layer may be applied to each of the rolled tape units to facilitate storage, dispensing, and mounting on the handheld device prior to actual use against the skin. Then, in such an embodiment, the non-tacky layer is removed thus exposing the tacky tape material 14.

In the past, tape stripping technology has been limited to use by professionally trained medical and cosmetic practitioners. At least one objective of this invention is to facilitate use by the individual user independent of the inconvenience, high cost, and lack of privacy implications of requiring office visits and the like in order to receive the benefits of this technology. Rather, as shown in FIG. 4, it is now possible to utilize the dispensing and individualized tape roller system disclosed in FIGS. 1-3 to allow individual users the chance to receive this treatment through self-administration. However, it is quite important to recognize that a methodology is recommended, and that such methodology has various options. As in most medical device, therapeutic, or other systems which relate to individual user preferences and morphology, there are various algorithms which apply to each individual user. FIG. 4 demonstrates an example of the algorithmic approach to use of this technology. While FIG. 4 provides an example of the program for a skin care treatment using the tape-stripping device of this invention, a program having essentially the same elements can be followed by patients using the handheld device with the removable treatment components having an abrasive material on the surface thereof which is also described herein.

Block 100 represents the proper first step or method, which requires careful assessment of the user's skin history, skin type, current skin condition, and usage goals of the system. After the user completes such proper assessment, he or she then selects the proper tape program according to the assessment of block 100. For example, one type of program (referred to herein as "P1") comprises a comprehensive rejuvenation program as later discussed below. Alternatively, a second tape program (referred to herein as "P2") comprises use of a tape-like material 14 having certain medications, such as an antibacterial material or a cortisone material imbedded in the tape and configured for release upon application to the skin. Yet another tape program (referred to herein as "P3") which may be appropriate for the particular user includes application of one or more elements to the skin following the initial tape application and removal. Such elements are also discussed below.

Following assessment of the skin and selection of the proper tape program according to the goals of the user, then the user applies the tape-like material 14 to the skin at the appropriate areas using, in one embodiment, the handheld device and roller system shown in FIG. 1. It is recognized that alternate dispensing means may be provided consistent with facilitating self-administration and ease of access to the various sites of interest on highly variable body morphologies. In a general sense however, this invention is designed to a great extent to facilitate the tape application to and removal from portions of a human facial skin area. Accordingly, a preferred ergonomic design may be found under the various options as shown in FIG. 1 to facilitate gripping in a comfortable manner, particularly at an early or late part of a user's day when the hand may be less comfortable or more stiff for various reasons.

Following application of the tape to the skin, a skin assessment is again recommended under the pathway R1 shown in FIG. 4. It is understood, however, that particularly experienced users may bypass the skin assessment at this point in the procedure. In this instance, pathway R2 directs the user to one of several program options P1, P2, or P3.

If the user selects tape program P1, then this program may include use of a cleanser 120, followed by a peel agent or toner 125, followed by an optional moisturizer 130, and then application of an activator 135. Examples of activators may include active lotions or materials such as those including vitamins or other rejuvenating elements. Alternatively, if the user selects tape program P2, then that user has chosen to utilize either a standard tape-like material 14 or a tape-like material 14 having additional medications imbedded or otherwise positioned on the tape. This latter configuration facilitates application of such medication while also removing the detritus or other tissue as discussed above during the same application of the tape. Regardless of which of the sub-options of step 140 of program 2 is selected, there is no need to proceed to any other substeps following application of the tape and removal of the tape from the skin.

However, if the user selects proper tape program P3 as shown at block 145, then the user may wish to follow-up the tape application and removal step with application of one of various types of elements, herein referred to as element X. For example, a topical anesthetic, a medication, a toning agent, a moisturizer, an activator, or even simply a cleanser, or even a splash of water may be appropriate for use as element X. It is also recognized that element X may also include a second application and/or subsequent applications of the tape to the skin within the context of this disclosure.

It is recognized therefore that system 10 is useful for dispensing tape means having various adhesive or tacky features on the tape. This tape is designed to remove excess skin cells or other material from the surface of skin in order to rejuvenate and stimulate that skin. A disposable single use type application is possible within the scope of this invention, and is quite appropriate in view of the increased environmental challenges and air particulate encountered every day by users. This self-administration product is particularly useful for home users for smoothing, refreshing, and regenerating damaged skin at a much lower cost than lasers, chemical peels or micro-derm abrasion. Indeed, the advantages of the embodiments of this technology shown in this application are quite distinct even over specific tape stripping by professional medical or cosmetic providers in a medical or cosmetic office environment. Regardless, no system exists for teaching and guiding the self user in the efficacious uses of a tape stripping system. This invention overcomes the failings of any prior art in providing simple and effective means for rejuvenating human skin in a manner appropriate to each individual user.

Further embodiments of handheld apparatus 10 may be configured in non-circular tape dispensing figurations, such as tape dispenser 163 shown in FIG. 5, having a tape-like product 14. The devices of the invention disclosed herein may also function as a rolling tape application motion, or as circular, or reciprocating, provided that the required skin to tape interface is achieved.

Figures 1, 11:
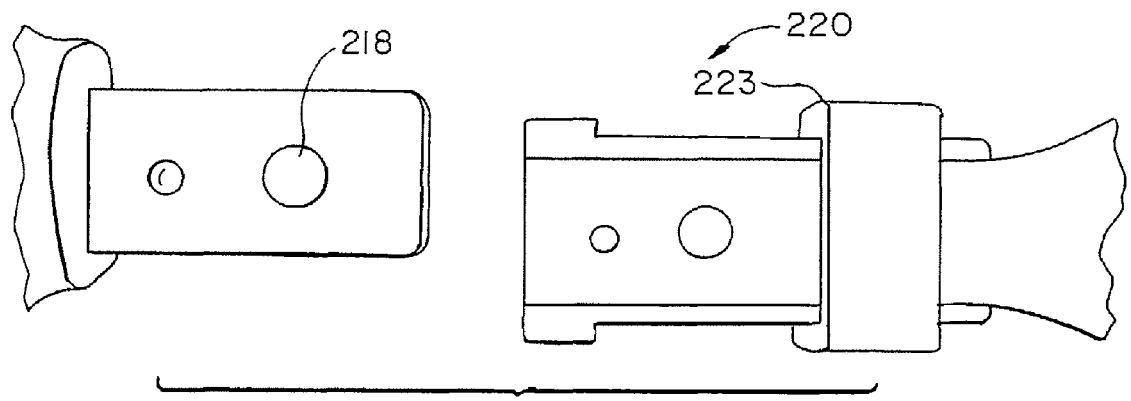
FIG. 11 is a side and plan view of a locking mechanism of the invention.
Figures 2, 11:
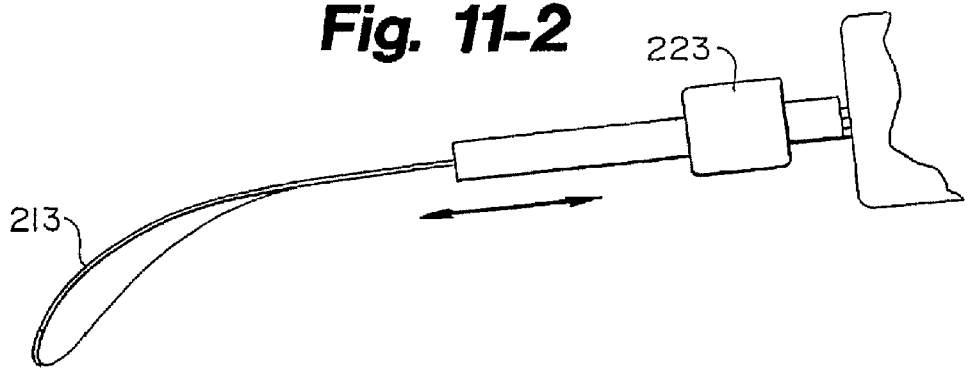
Figures 3, 11:
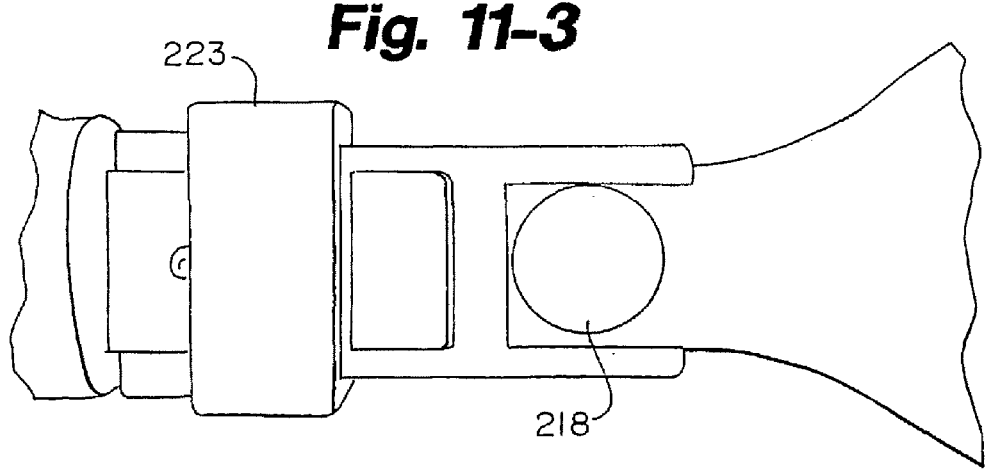

FIGS. 6 and 7 illustrate an embodiment of the invention comprising handheld apparatus 200. Handheld apparatus 200 is designed to provide an ergonomic gripping handle 204, having an internal motion generator, generally of conventional type similar to that found in mechanical or electrical toothbrush mechanisms, but with a capability of causing or imparting motion to an applicator tip or treatment component 213 connected to the distal surface of the apparatus through a connection element (shown as 215 in FIG. 11). The treatment component 213 may be configured so that it is removable and reconfigurable, as desired.

In one embodiment, treatment component 213 has a first portion 214 designed for connection with an motion generating subsystem of the internal motion generator of the handle and a second portion 216 having a shaped configuration and a first and second surface, wherein the second portion is configured so that the first surface will conform to a skin surface and wherein said first surface comprises an abrasive material formed in or attached to the surface. The first surface 217 comprises an abrasive material formed in or attached thereto where the abrasive material is chosen to effect cleaning, abrading, or polishing of the skin surface as the treatment component moves over the surface of the skin.

The abrasive material may be an abrasive element such as sand, aluminum oxide silica, etc., a metallic material into which a pattern has been etched or stamped such as metallic materials like gold, silver, platinum or crystal particles such as glass, sapphire, alexandrite, etc. The material may be etched, stamped or otherwise be formed as part of the treatment component surface or it could be a thin metal, fabric, plastic, rubber film on which the abrasive material has been etched, stamped or affixed on to it and adhered to the surface of the treatment component using any known adhesive.

In operation, device 200 is held by the user while the treatment component 213, having an appropriate abrasion characteristics attached to the distal tip of the handheld device is pressed onto the skin surface. The user activates the motion of the treatment component 213 using various activation means such as, for example, activating mechanism 221. Following activation, component 213 is set in motion in either a reciprocating, circular or other fashion so as to effect the appropriate abrasion using the abrasive material on the user's skin.

As shown in FIG. 6, one embodiment of this device includes a charging stand which comprises a power element adapted to connect with connectors carried in the handheld device that will recharge the rechargeable battery within the gripping portion of the device when the device is placed in the stand. Yet another embodiment includes, for example, a device which does not have the internal mechanisms described herein above in relation to this handheld device but rather has a remote connection, such a wired connection, with a remotely configured motor or motion generator which may be selectively applied by cord or wireless to the handheld device and the drive means located within the handheld device, thereby imparting power for the motion of treatment component 213 independent of the possible cumbersome size of an internally located motion generating mechanism.

Figure 10:
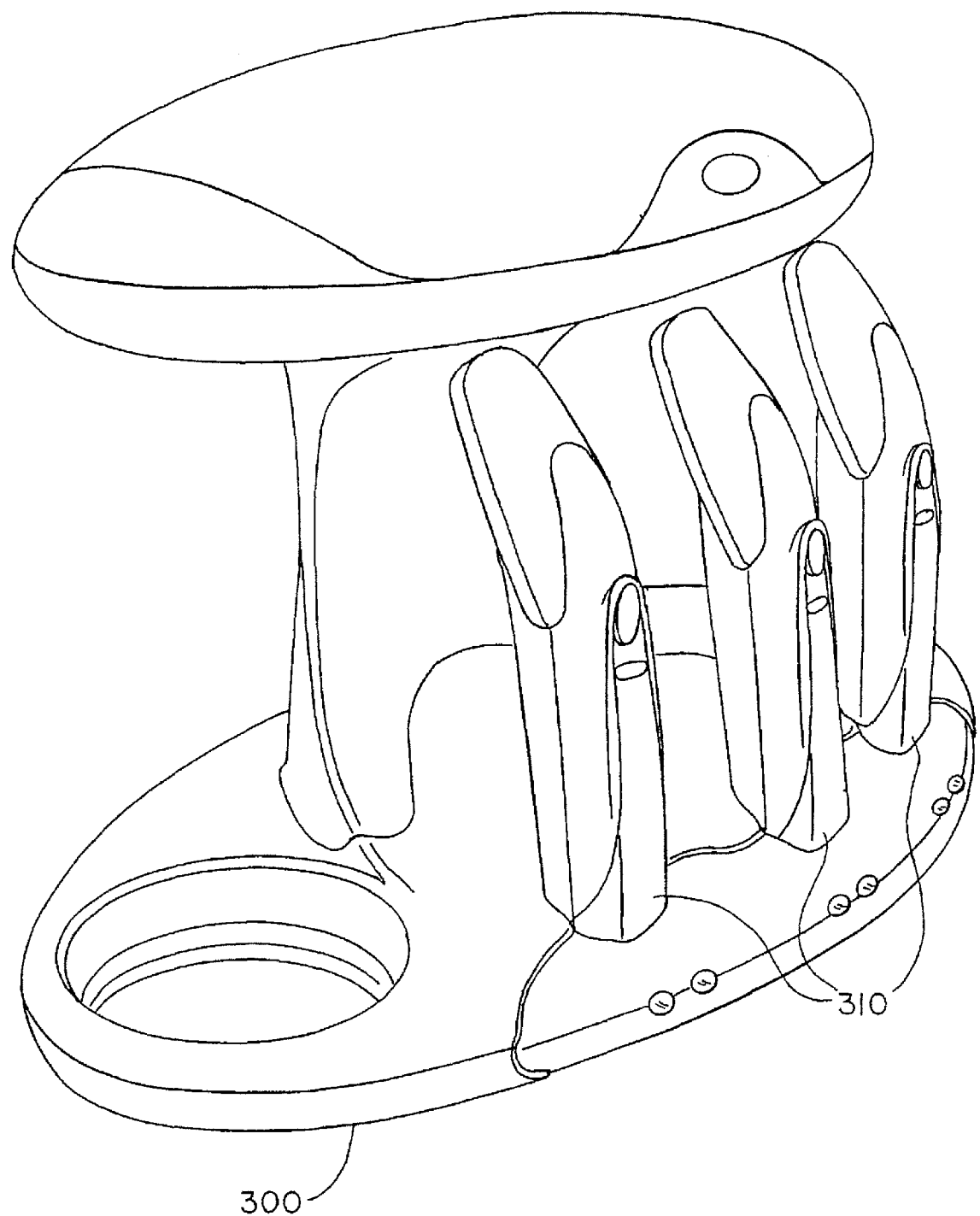
FIG. 10 is a view of a stand of the invention showing a container for the treatment components and receptacles for the handheld device.

In FIG. 10, an embodiment of the charging stand 300 is shown comprising a plurality of receptacles 310 each having a power element adapted to connect with connectors carried in a handheld device that will recharge the rechargeable battery of a device when placed in the receptacle.

A charging stand could be adapted to be used with multiple handheld devices that are used for skin treatment by professionals or self-application. A charging stand may include a receptacle for the tape-stripping handheld apparatus shown in FIG. 1 and a separate receptacle for the handheld apparatus with the removable treatment component shown in FIG. 7. The skin care program shown in FIG. 4, could be adapted to be used with either or both devices. Additionally, handheld devices with other treatment modalities that may be adapted for use in a total skin care program could be included with the same recharging base. Such devices may include a transcutaneous electrical nerve stimulator adapted for facial stimulation, an ultrasound device adapted for stimulation of skin of about 20-30 K hertz, a laser for skin resurfacing and/or non-coherent light device for biostimulation.

In yet another embodiment of the invention, the system includes a locking mechanism for locking the treatment component to the connection element located on the distal tip surface of the handheld device. This locking mechanism is desirably connected to the drive means located within the handheld device and/or the motion generator in such a way that the device cannot be operated unless an appropriate treatment component is locked into place. The locking mechanism can be any known locking mechanism. In one embodiment shown in three views in FIG. 11 the locking mechanism 220 may include an aperture 218 defined in either the connection element 215 or the portion of the treatment component designed for connection with a motion generating subsystem of the internal motion generator and a protrusion 219 in the matching piece of the connection element or treatment component. The motion generating subsystem is desirably part of the drive means located at the distal end of the handheld device. When the treatment component 213 is attached to the handheld device, the protrusion 219 will fit through the aperture 218 as shown in view 3 of FIG. 11 preventing the pieces from separating if the user tugs on the treatment component. In order to prevent the two pieces from separating a slideable element 223 located on either piece can be slipped into place covering the connection and preventing the pieces from separating as shown in view 2. The slideable element may be connected electronically to the motion generator through an actuatable motion generator and control element so that when it is in place this handheld device may be activated.

Figures 1, 12:
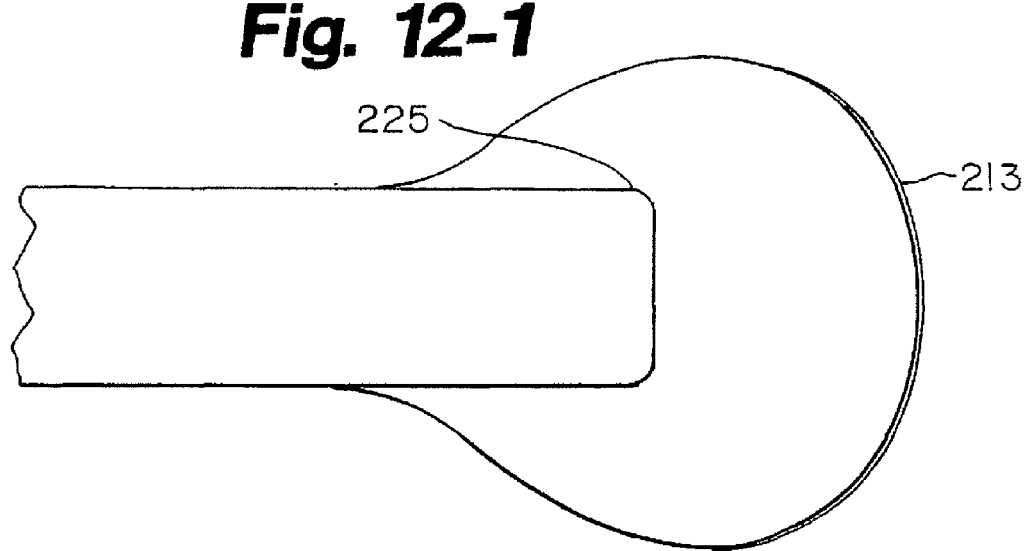
FIG. 12 is a side and plan view of a pressure sensitive circuit switch of a treatment component of the invention.
Figures 2, 12:
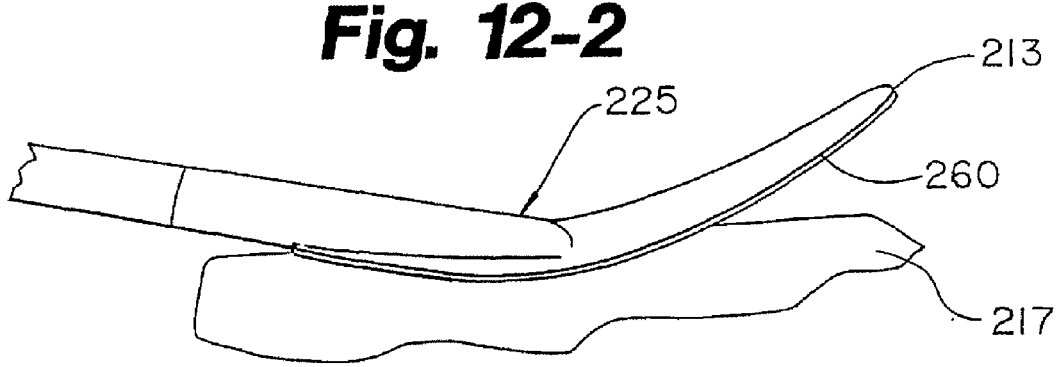
Figures 3, 12:
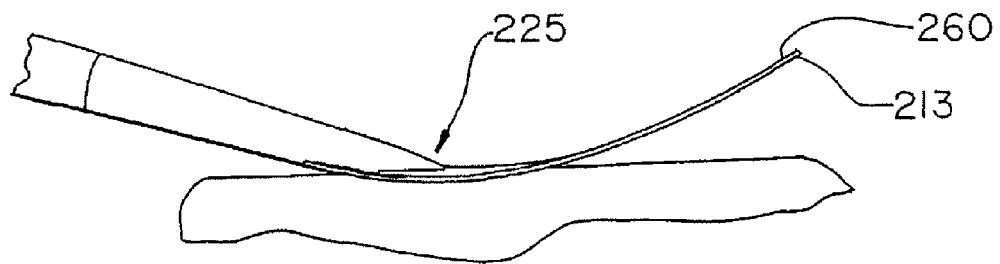

In another embodiment of the invention, the system includes a stand for the handheld device which includes an external power source and actuatable motion generator and control element. The control element may include feedback means which may be used to monitor the pressure applied to the treatment component surface when it is pressed upon the skin through electrical connections. FIG. 12 shows three views of a pressure sensitive circuit which may be used for monitoring the pressure applied to the treatment component surface when it is pressed upon the surface of the skin. At the distal portion 250 of the first portion 214 of the treatment component 213 a pressure element 255 will protrude from the first portion of the treatment component so that it is spaced above the concave surface 260 of the treatment component 213 a predetermined distance as shown in view 2 so that when sufficient pressure is applied to the treatment component as it is pressed upon the skin, the treatment component with the treatment surface will bend back and touch the pressure element as shown in view 3 in FIG. 12. View 1 shows a plan view of the treatment component with the pressure element 255 above the concave surface. An electrical circuit, not shown, may be connected to the pressure element so that when the treatment component and pressure element touch an alarm is sounded or the device switches off.

In yet another embodiment of the invention, the actuatable motion generator and control element may be connected to a timer, not shown, which will measure the amount of time the treatment component is activated and at predetermined time intervals will generate a signal to notify the user that the predetermined interval of time has passed. The signal may be a sound, a light or the device may turn off at the appropriate time.

In yet another embodiment, a display is located either in the body of the handheld device, not shown, or is incorporated into the stand 265 for the device as shown in FIG. 13. The display 270 may be of any type such as a LCD, or a series of lights or colored lights. The display be connected to the timer and may simply display the time the device has been in operation or it may be in the shape of a human body as shown in FIG. 13 with portions of the body being depicted in some manner. When a certain predetermined interval of time has passed one portion of the body may light up, or change colors or if the entire body is lit, one portion could go black to signal to the user that that portion of the body has been treated during that time interval. The display may be attached through sensors to the treatment component in such a way that the area of the body being treated can be sensed through the sensors and the appropriate portion of the display illuminated to show where the treatment has occurred. Alternately, the display may be used in connection with the program for treatment described above and used to help lead the user through the treatment process.

In one embodiment of the invention, a skin treatment program is designed using a device such as that shown in FIG. 7, wherein the treatment protocol comprises the following: the skin surface to be treated is cleansed and a toner is applied, then the handheld device of the invention is used with a treatment component having an abrasive material applied to the one surface. The motion of the treatment component is activated and the skin surface is treated for one to ten minutes or until the skin's surface appears smooth or sufficient layers of skin are removed or dislodged from the surface. The same area of skin is treated weekly for six weeks and in between treatments the client will follow a detailed skin care program suggested for use with the treatments. After the sixth treatment the client continues to follow the home skin care program and returns for further treatment.

Figure 9:
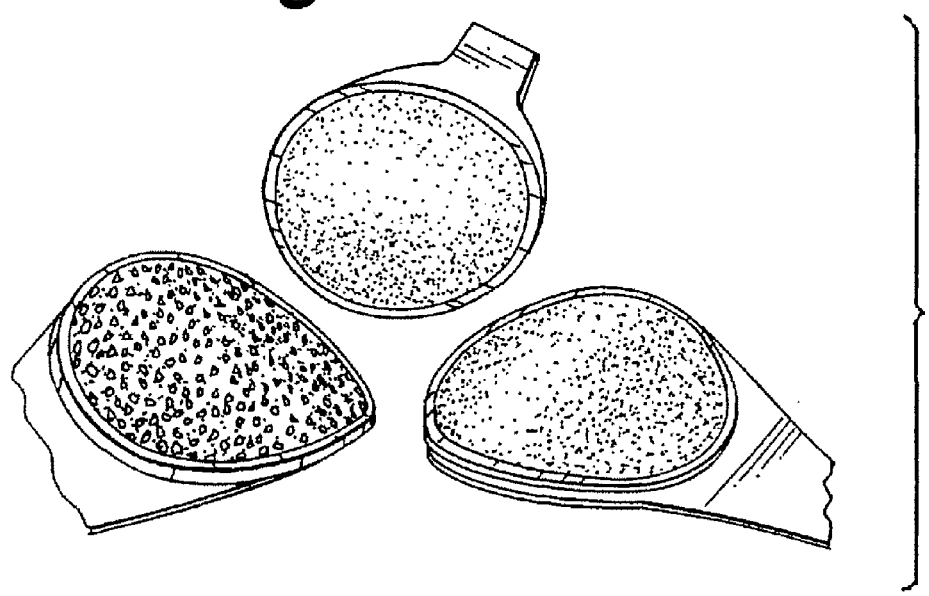
FIG. 9 shows three degrees of exfoliation texture of abrasive material as applied to the surface of treatment components of the invention.

The handheld device of this invention shown in FIG. 7, with a treatment component such having moderate abrasive material on the conforming surface as shown in FIG. 9 was used in a histologic study of two subjects having sun damaged skin on the dorsal forearm. The subject each treated him/herself daily for a fourteen day period. The treatment component was pressed onto the skin surface, and the motion activated so that the treatment component moved back and forth horizontally over the skin surface. The treatment consisted of two to eight passes of the treatment component over the skin. Each pass is one back and forth motion.

After the treatments were completed biopsies of the treated skin were taken and examined with light microscopy, electron microscopy and immunohistochemistry to see if any changes had occurred in the skin in collagen production. In-situ hybridization studies were done to detect Type I collagen mRNA, the presence of which is correlated to the translation of the protein Type I collagen. The studies showed that the treated skin had a normalization of the sun damage with thickening of the epidermis, increased Type I and III collagen formation in the superficial dermis and increased Type I collagen mRNA in fibroblasts in the superficial epidermis.

In a comparative study between treatment with the handheld device of the invention with the treatment component having an abrasive material on the surface being used in the treatment and treatment with microdermabrasion the device of the invention resulted in less redness and edema and client discomfort. A licensed professional performed this study. Each subject was given six treatments at weekly intervals, using the treatment component with the moderate abrasive material, light pressure with four passes per area on one side of the face and a Parisian peel microdermabrader set at 20 psi used to treat the other side of the face using two to four passes. In the study, ninety percent of the clients treated with microdermabrasion reported redness and twenty-five percent of them reported edema in the treated area. None of the clients treated with the device and method of the invention reported any redness or edema.

While the systems or the invention may be used in connection with creams the abrasive material is not in the cream it is part of a treatment component or part of a tape strip. This provides the user with better control over the amount of abrasion obtained during the treatment. Furthermore, the system of the invention is less messy and there is less concern with having abrasive material get into the client's eyes. When the system of the invention is used with the treatment components, the motion of the treatment component can be adjusted so that not only is the surface of the skin being abraded but the top layer of skin, the stratum corneum, is stimulated or altered in such a manner that alterations in the deeper layers of the skin are observed, such as thickening of the epidermis and the stimulation of the production of dermal ground substances such as collagen in the dermis. These changes in the skin layers were observed in histological studies performed on tissue samples of client's skin following treatment with the system of the invention. It has also been appreciated by the inventors that the system, device components, and methods described above are useful for hair removal, drug delivery, and serum extraction for diagnostic and related purposes. Accordingly, the disclosure of the invention contemplates claims to these aspects of the invention as well.

What is claimed is:

1. A skin abrasion system for facilitating removal of tissue from the surface of a user's skin, comprising: an ergonomically shaped handheld device having an internal motion generator for imparting reciprocating motion to a removable treatment component at a distal tip thereof, a pressure sensitive circuit associated with the treatment component in such a way that during use, if the user places the treatment component against the skin with greater than a predetermined pressure, the circuit is triggered and a signal generated, and a distal tip surface comprising a connection element for connecting the treatment component with said distal tip, and a hand actuatable motion generator and control element; and the treatment component having a first portion designed for connection with a motion generating subsystem of the internal motion generator through the connection element and a second portion having a shaped configuration and a first and second surface, wherein the second portion is configured so that the first surface will conform to a skin surface and wherein said first surface comprises an abrasive material attached to the surface and which when applied to and moved on the skin will effect cleaning, abrasion or polishing of the skin to facilitate removal of tissue.

2. The system of claim 1 wherein the treatment component may be chosen from a plurality of treatment components each having the first portion designed for connection with the motion generating subsystem of the handheld device and a second portion having a shaped configuration of a predetermined surface area, wherein the predetermined surface area of each treatment component is different from any other treatment component in the plurality of treatment components.

3. The system of claim 1 wherein the handheld device further comprises a switch that allows the treatment component to move in a reciprocating motion when the treatment component is connected to the motion generating subsystem.

4. The system of claim 1 wherein the signal generated by the pressure sensitive circuit switches off the actuatable motion generator and control element and stops the motion of the treatment component.

5. The system of claim 1 wherein the actuatable motion generator and control element is disposed within a stand on which the handheld device and treatment component may be stored when not in use.

6. The system of claim 5 wherein the actuatable motion generator and control element includes a feedback system capable of sending and receiving signals to and from the treatment component during its use which signals control the speed and direction of the treatment component.

7. The system of claim 1 wherein the actuatable motion generator and control element further includes a timer that will keep track of the time that the treatment component is in motion and will signal the user when the treatment component has been moving for a predetermined period of time so that the user can choose to move the treatment component to another area of skin for treatment for the next measured time interval.

8. The system of claim 7 wherein the actuatable motion generator and control element is connected to a display located either on the handheld device or on a stand in which the actuatable motion generator and control element is disposed, the display being arranged so that as the timer signals to the user that the treatment component has been moving for a predetermined period of time a portion of the display is illuminated so the user can keep track of how many_time intervals have passed.

9. The system of claim 8 wherein the display is in the shape of a human body and with each signal of the timer a different portion of the display is illuminated so that the user can apply the treatment components to the appropriate portions of the body for predetermined time intervals.

10. A skin abrasion system for facilitating removal of tissue from the surface of a user's skin, comprising: an ergonomically shaped handheld device comprising an internal motion generator for imparting reciprocating_ motion to a treatment component insertable at a distal tip thereof, a distal tip surface comprising a connection element for removably connecting the treatment component to the handheld device, and an actuatable motion generator and control element connected to the internal motion generator; the treatment component having a first portion designed for insertion into a motion generating subsystem through the connection element of the distal tip surface, and a second portion having a shaped configuration and a first and second surface, wherein the second portion is configured so that the first surface will conform to a skin surface and wherein said first surface comprises an abrasive material formed in or attached to the surface and the abrasive material is chosen for its ability to effect cleaning, abrading or polishing of the user's skin when the motion of the treatment component is activated and the treatment component is pressed onto the skin's surface.

11. A skin abrasion system for facilitating removal of tissue from the surface of a user's skin, comprising: an ergonomically shaped handheld device comprising an internal motion generator for imparting reciprocating_ motion to a removable treatment component at a distal tip thereof, and a distal tip surface having a connection element for connecting the treatment component portion to said distal tip, and a handheld hand actuatable motion generator and control element; the treatment component having a first portion designed for connection with a motion generator subsystem of the internal motion generator through the connection element, and a second portion having a shaped configuration and a first and second surface, wherein the second portion is configured so that the first surface will conform to a skin surface and wherein said first surface comprises an abrasive material formed in or attached to the surface and the abrasive material is chosen for its ability to effect abrasion or polishing of the user's skin to facilitate removal of tissue when the treatment component is activated; and wherein the actuatable motion generator and control element is powered by a rechargeable battery disposed within the handheld device.

12. The system of claim 11 further comprising a charging stand which includes electric generator for charging the rechargeable battery.

13. The system of claim 12 wherein the charging stand comprises receptacles for charging the rechargeable batteries of a plurality of handheld devices.

14. A skin abrasion system for facilitating removal of tissue from the surface of a user's skin, comprising: an ergonomically shaped handheld device comprising an internal motion generator for imparting reciprocating motion to a distal treatment component at a distal tip thereof, and a distal tip surface having a connection element for connecting the treatment component with said distal tip, and an actuatable motion generator and control element; the treatment component having a first portion designed for connection with a motion generating subsystem of the internal motion generator through the connection element, and a second portion having a shaped configuration and a first and second surface, wherein the second portion is configured so that the first surface will conform to a skin surface and wherein said first surface comprises an abrasive material formed in or attached to the surface and the abrasive material is chosen for its ability to effect abrasion or polishing of the user's skin; and wherein the actuatable motion generator and control element is powered by an external power source connected to the handheld device through a cord.

\* \* \* \* \*